United States Patent [19]

Halcour et al.

[11] 4,244,877
[45] Jan. 13, 1981

[54] PROCESS FOR THE PREPARATION OF HEXAHYDROPHTHALIC ACID ANHYDRIDE

[75] Inventors: Kurt Halcour; Helmut Waldmann; Wulf Schwerdtel, all of Leverkusen, Fed. Rep. of Germany

[73] Assignee: Bayer Aktiengesellschaft, Leverkusen, Fed. Rep. of Germany

[21] Appl. No.: 41,547

[22] Filed: May 23, 1979

[51] Int. Cl.³ ............................................. C07D 307/89
[52] U.S. Cl. .................................. 260/346.3; 260/546; 260/346.6; 260/346.7
[58] Field of Search ................. 260/546, 346.3, 346.6, 260/346.7

[56] References Cited

U.S. PATENT DOCUMENTS

| | | | |
|---|---|---|---|
| 2,601,075 | 6/1952 | Wichlaty et al. | 260/346.6 |
| 2,794,811 | 6/1957 | Winstrom | 260/346.3 |
| 3,169,975 | 2/1965 | Schulz | 260/346.3 |
| 3,819,658 | 6/1974 | Gormley et al. | 260/346.3 |
| 3,957,688 | 5/1976 | Farha et al. | 252/466 PZ |

*Primary Examiner*—James H. Reamer
*Attorney, Agent, or Firm*—Connolly and Hutz

[57] ABSTRACT

A process for the preparation of hexahydrophthalic acid anhydride which comprises hydrogenation $\Delta^4$-tetrahydrophthalic acid anhydride in the liquid phase at a temperature of from 70° to 150° C. and at a pressure of from 30 to 200 bar in the presence of a catalyst selected from palladium, ruthenium, nickel or mixtures thereof arranged in a fixed bed, wherein the catalyst is applied to a carrier of alumina of which at least 20% by weight has been converted into lithium aluminium spinel and the liquid phase is a mixture of $\Delta^4$-tetrahydrophthalic acid anhydride and hexahydrophthalic anhydride in a proportion by weight of from 1:1 to 1:100.

12 Claims, No Drawings

PROCESS FOR THE PREPARATION OF HEXAHYDROPHTHALIC ACID ANHYDRIDE

The present invention relates to a process for the hydrogenation of $\Delta^4$-tetrahydrophthalic acid anhydride to hexahydrophthalic acid anhydride without the use of a foreign solvent, in a trickle phase or flood phase over a fixed bed catalyst of palladium and/or ruthenium and/or nickel applied to a carrier of alumina of which at least 20% has been converted into lithium-aluminium spinel.

The hydrogenation of $\Delta^4$-tetrahydrophthalic acid anhydride to hexahydrophthalic acid anhydride is known.

In the known process, the tetrahydrophthalic acid anhydride is in most cases dissolved in a foreign solvent. According to U.S. Pat. No. 2,601,075, for example, tetrahydrophthalic acid anhydride is dissolved in ethyl acetate, and according to J.Amer.Chem.Soc. Vol. 60 (1938) page 2145 it is dissolved in glacial acetic acid and the hydrogenation catalyst, which is either Raney nickel or finely divided platinum black (according to Adam), is suspended and hydrogenation is then carried out. One disadvantage of this known type of process is that the foreign solvent and the catalyst must subsequently be removed from the hydrogenated product. Another disadvantage lies in the excessively long hydrogenation times needed.

According to U.S. Pat. No. 2,794,811, $\Delta^4$-tetrahydrophthalic acid anhydride is hydrogenated to hexahydrophthalic acid anhydride in the solvent free state in the presence of suspended nickel catalyst which is precipitated on silica. In this process it is also necessary to separate the catalyst by filtration or else to employ long settling times after which the hydrogenated product may be separated from the settled catalyst. This process also requires relatively long hydrogenation times.

According to U.S. Pat. No. 3,169,975 unsaturated carboxylic acid anhydrides such as maleic acid anhydride or tetrahydrophthalic acid anhydride can be continuously converted into the corresponding saturated carboxylic acid anhydrides by the trickle process carried out in the liquid phase, i.e. using foreign solvent or in the molten solvent free state, by catalytic hydrogenation with copper, cobalt or nickel molybdates, tungstates, chromates or vanadates arranged in a fixed bed. In the case of tetrahydrophthalic acid anhydride, however, hydrogenation is carried out in dioxane as a foreign solvent. Another disadvantage of this method is the high catalyst content required, which according to the examples given in the said Patent Specification amounts to about 10 to 20% by weight, based on the impregnated carrier material.

It is an object of the present invention to hydrogenate $\Delta^4$-tetrahydrophthalic acid anhydride continuously, virtually quantitatively and in high volume/time yields to hexahydrophthalic acid anhydride. It is intended that the process should operate economically and obviate the disadvantages of the known processes described above.

It has now been found that carrying out the hydrogenation in the liquid (i.e. trickle or flood phase) using specific catalysts on special carriers in a fixed bed and, preferably, using the hydrogenated product as solvent overcomes the above disadvantages.

Accordingly, the present invention provides a process for the preparation of hexahydrophthalic acid anhydride which comprises hydrogenation $\Delta^4$-tetrahydrophthalic acid anhydride in the liquid phase at a temperature of from 70° to 150° C. and at a pressure of from 30 to 200 bar in the presence of a catalyst selected from palladium, ruthenium, nickel or mixtures thereof arranged in a fixed bed, wherein the catalyst is applied to a carrier of alumina of which at least 20% by weight has been converted into lithium aluminium spinel and the liquid phase is a mixture of $\Delta^4$-tetrahydrophthalic acid anhydride and hexahydrophthalic anhydride in a proportion by weight of from 1:1 to 1:100.

The tetrahydrophthalic acid anhydride used as starting material may be obtained in known manner by, for example, synthesis from butadiene and maleic acid anhydride (Diels-Alder diene synthesis), the product being obtained mainly as the cis-$\Delta^4$-isomer.

Hydrogenation in the present invention is carried out in the trickle or flood phase on catalysts arranged in a fixed bed in a suitable hydrogenation apparatus.

The catalyst arranged in the fixed bed may be introduced into a shaft furnace but for the sake of removal of heat it is preferably introduced into a reactor in the form of a nest of tubes surrounded by a stream of heat transfer medium.

As previously stated, hydrogenation may be carried out in the trickle phase or flood phase. In the trickle phase, the substance to be hydrogenated trickles through the reactor downwards from above and over the catalyst which is situated in a hydrogen atmosphere. The hydrogen may be introduced into the reactor either from above or from below. Part of the exhaust is generally released into the atmosphere after separation of the liquid product. If hydrogenation is carried out in the flood phase, the starting materials and hydrogen, usually in the dissolved form, flow upwards through the catalyst bed from below. The time required for hydrogenation in the trickle phase depends upon the length of the reactor. In a reactor having a length of 6 meters, it is less than 10 minutes. In the flood phase, the hydrogenation time depends on both the quantity of starting material and the length of the reactor, but is at the most, generally, one hour.

Although the hydrogenation of $\Delta^4$-tetrahydrophthalic acid anhydride may in principle be carried out in the undiluted form, i.e. in the solvent-free state, it has been found extremely advantageous to use the hexahydrophthalic acid anhydride obtained as reaction product as diluent because this not only reduces the localised evolution of heat but may also lower the melting point of the starting mixture from about 102° C. to 40° to 60° C. It is, of course, unnecessary to separate the diluent from the hydrogenation product since it is identical with it. Part of the hydrogenation product may be directly pumped back to dilute the $\Delta^4$-tetrahydrophthalic acid anhydride starting material. In this case, the proportion by weight of hexahydrophthalic acid anydride to 4-tetrahydrophthalic acid anhydric used is in the range of from 1:1 to 1:100, preferably from 1:5 to 1:30.

Either hydrogen or gases containing hydrogen may be used for the hydrogenation. Any catalyst poisons contained in the hydrogenation gases must first be removed. After the hydrogenation reaction, a small proportion of the residual gas may be released from pressure in order to prevent the accumulation of inert gases.

Special catalysts are advantageous for the hydrogenation of $\Delta^4$-tetrahydrophthalic acid anhydride to, preferably, cis-hexahydrophthalic acid anhydride by the process according to the invention. Palladium and/or ruthenium and/or nickel are used, preferably palladium and/or ruthenium and most preferably palladium alone.

The catalyst is, generally, applied to the carrier in an amount of from 0.1 to 5% by weight. The catalyst carrier used is an alumina of which at least 20% has been converted into lithium aluminum spinel. The catalyst carrier may be in a cylindrical form, in the form of an extrudate or in a pelletised form or as lumps, but it is preferably in the form of spherical particles (preferably having a diameter of approx. 1 to 8 mm).

Hydrogenation in the liquid phase is carried out at pressures of from 30 to 200 bars. Pressures of from 50 to 200 bar, preferably from 80 to 150 bar are generally employed.

The temperatures for hydrogenation of $\Delta^4$-tetrahydrophthalic acid anhydrides should be in the range of from 70° to 150° C., preferably in the range of from 90° to 110° C.

The volume/time yield may be, e.g., from 0.1 to 5 kg of hexahydrophthalic acid anhydride per liter of catalyst (=catalyst+catalyst carrier) an hour, preferably below 2 kg/l an hour.

Hexahydrophthalic acid anhydride may be used as a hardener for 1,2-polyepoxides and/or as an intermediate product for the production of synthetic resins such as polyepoxide resins and polyester resins.

The process according to the present invention is described in more detail with the aid of the examples given below. The percentage contents given are based on weight unless otherwise indicated.

DESCRIPTION OF THE HYDROGENATION APPARATUS

The reactor used with a tube either 4 or 6 m long having an internal width of 24 mm. It was enclosed in a double jacket which could be heated with steam and cooled with condensate. The catalyst was fixed inside the reactor tube. In the case of trickle phase hydrogenation, the starting material to be hydrogenated, diluted with returned hydrogenation product, was passed over the catalyst from above.

A separator from separating liquid reaction product from residual gas was situated at the lower end of the reactor. In most cases, a part of the reaction product was pumped back for use and the remainder was released into the atmosphere. Hydrogen was introduced under pressure at the upper end of the reactor together with the liquid starting material while a small quantity, amounting throughout to 10% of the theoretically required quantity of hydrogen gas was released as exhaust gas from the separator situated under the reactor.

Hydrogenation in the flood phase was carried out in the same reactor as that used for trickle phase hydrogenation. Hydrogen and the component to be hydrogenated (diluted with the hydrogenation product) were introduced under pressure at the lower end of the reactor. The separator for separating gaseous and liquid phase, and from which the products were released in the case of the trickle phase, was situated at the top end of the reactor.

CATALYSTS

The catalysts used were palladium, ruthenium and nickel or combinations thereof applied to lithium aluminium spinel as catalyst carrier.

The preparation of the catalyst carrier is described below by way of example:

2.86 Liters of spherical $\gamma$-alumina measuring either 1 to 3 mm or 4 to 6 mm in diameter and having an internal surface area of ca. 250 m$^2$/g were impregnated at 30° C. with 1 liter of aqueous solution to which had been added successively 296 g of formic acid and 233 g of a 54% aqueous lithium hydroxide solution. The impregnated alumina was dried in a vacuum at 150° C., again impregnated with the same solution and again dried in a vacuum at 150° C. The carrier was then annealed for 6 hours at 1050° C. to convert it into the lithium aluminum spinel, the structure of which was confirmed by X-ray photography (60% spinel). The finished carrier has an internal surface area of ca. 30 m$^2$/g and an average pore size of ca. 700 Å.

Application of the noble metals was carried out by the usual method of impregnation with aqueous solutions of the noble metal salts, reduction, washing (to free from anions) and drying. Catalysts (=catalyst+catalyst carrier) containing the following quantities of noble metal were prepared in this way:

| Catalyst No. | % noble metal |
| --- | --- |
| 1 | 1% Pd |
| 2 | 1% Ru |
| 3 | 0.5% Pd 0.5% Ru |
| 4 | 5% Ni |

HYDROGENATION EXAMPLE 1

Tetrahydrophthalic acid anhydride diluted with hexahydrophthalic acid anhydride (1:10) was continuously hydrogenated in the trickle phase at a pressure of 100 bar and a temperature of 105° C. over 3 liters of catalyst No. 1 in the hydrogenation apparatus described above. A volume/time yield of 1 kg of hexahydrophthalic acid anhydride per liter of catalyst an hour was obtained. 400 Nl/h exhaust gas (Nl=liter under normal conditions) were released from the separator. The yield of hexahydrophthalic acid anhydride was over 99%. Virtually no hexahydrophthalic acid and hexahydrophthalide were formed as by-products.

HYDROGENATION EXAMPLE 2

When catalyst No. 2 were used instead of catalyst No. 1 under the same conditions as used in Example 1, a 99.5% yield in hexahydrophthalic acid anhydride was obtained and hexahydrophthalide occured as by-product.

HYDROGENATION EXAMPLE 3

Undiluted tetrahydrophthalic acid anhydride was continuously hydrogenated in the trickle phase over 3 liters of catalyst No. 3 at a pressure of 120 bar and a temperature of 95° C. A volume/time yield of 800 g per liter of catalyst an hour was achieved. 400 Nl of exhaust gas per hour were released from the separator. The yield of hexahydrophthalic acid anhydride was 99.2%. A small amount of hexahydrophthalide was formed as by-product.

HYDROGENATION EXAMPLE 4

Tetrahydrophthalic acid anhydride was diluted with hexahydrophthalic acid anhydride in a proportion of 1:6. Hydrogenation was carried out continuously in the flood phase over 3 liters of catalyst No. 4 at a pressure of 120 bar and a temperature of 100° C. in the apparatus described above. A volume/time yield of 1.0 kg of hexahydrophthalic acid anhydride per liter of catalyst an hour was achieved. Exhaust gas was released from the separator at the rate of ca. 800 Nl/h. The yield of hexahydrophthalic acid anhydride was 99%. Hexahydrophthalide and hexahydrophthalic acid were the only by-products.

We claim:

1. A process for the preparation of hexahydrophthalic acid anhydride which comprises hydrogenation $\Delta^4$-tetrahydrophthalic acid anhydride in the liquid phase at a temperature of from 70° to 150° C. and at a pressure of from 30 to 200 bar in the presence of a catalyst selected from palladium, ruthenium, nickel or mixtures thereof arranged in a fixed bed, wherein the catalyst is applied to a carrier of alumina of which at least 20% by weight has been converted into lithium aluminum spinel and the liquid phase is a mixture of $\Delta^4$-tetrahydrophthalic acid anhydride and hexahydrophthalic anhydride in a proportion by weight of from 1:1 to 1:100.

2. A process as claimed in claim 1 wherein the liquid phase is a mixture of $\Delta^4$-tetrahydrophthalic acid annydride and hexahydrophthalic anhydride in a proportion by weight of from 1:5 to 1:30.

3. A process as claimed in claim 1 wherein the hydrogenation is carried out at a temperature of from 90° to 110° C.

4. A process as claimed in claim 1 wherein the hydrogenation is carried out at a pressure of from 50 to 200 bar.

5. A process as claimed in claim 4 wherein the hydrogenation is carried out at a pressure of from 80 to 150 bar.

6. A process as claimed in claim 1 wherein the catalyst is selected from palladium, ruthenium or mixtures thereof.

7. A process as claimed in claim 1 wherein the catalyst is palladium.

8. A process as claimed in claim 1 wherein the carrier is in the form of spherical particles.

9. A process as claimed in claim 8 wherein the particles have a diameter of from 1 to 8 mm.

10. A process as claimed in claim 1 wherein the catalyst is applied to the carrier in an amount of from 0.1 to 5% by weight.

11. A process as claimed in claim 1 wherein the liquid phase is the trickle phase.

12. A process as claimed in claim 1 wherein the liquid phase is the flood phase.

* * * * *